United States Patent
Sakamoto et al.

(10) Patent No.: US 12,139,615 B2
(45) Date of Patent: Nov. 12, 2024

(54) METHOD FOR PRODUCING HALOGENATED ZINC PHTHALOCYANINE PIGMENT

(71) Applicant: DIC Corporation, Tokyo (JP)

(72) Inventors: Keisuke Sakamoto, Sakura (JP); Kentaro Oishi, Sakura (JP); Ryousuke Asami, Sakura (JP); Mayumi Tokuoka, Kamisu (JP); Katsunori Shimada, Sakura (JP)

(73) Assignee: DIC CORPORATION, Tokyo (JP)

( * ) Notice: Subject to any disclaimer, the term of this patent is extended or adjusted under 35 U.S.C. 154(b) by 801 days.

(21) Appl. No.: 17/296,656

(22) PCT Filed: Apr. 30, 2020

(86) PCT No.: PCT/JP2020/018352
§ 371 (c)(1),
(2) Date: May 25, 2021

(87) PCT Pub. No.: WO2021/220497
PCT Pub. Date: Nov. 4, 2021

(65) Prior Publication Data
US 2023/0144572 A1     May 11, 2023

(51) Int. Cl.
*C07D 487/22* (2006.01)
*C09B 47/10* (2006.01)
*C09B 67/20* (2006.01)

(52) U.S. Cl.
CPC ............ *C09B 47/10* (2013.01); *C07D 487/22* (2013.01); *C09B 67/0066* (2013.01)

(58) Field of Classification Search
CPC .................................. C07D 487/22
See application file for complete search history.

(56) References Cited

U.S. PATENT DOCUMENTS

| | | |
|---|---|---|
| 2006/0060111 A1 | 3/2006 | Ganschow et al. |
| 2016/0090484 A1 | 3/2016 | Sato et al. |
| 2022/0002550 A1* | 1/2022 | Sakamoto ............... C09B 47/10 |

FOREIGN PATENT DOCUMENTS

| | | |
|---|---|---|
| CN | 1572841 A | 2/2005 |
| CN | 1329455 C | 8/2007 |
| CN | 102786814 A | 11/2012 |
| CN | 105209553 A | 12/2015 |
| CN | 106716190 A | 5/2017 |
| CN | 108070279 A | 5/2018 |
| CN | 109563355 A | 4/2019 |
| CN | 109642970 A | 4/2019 |
| CN | 109863208 A | 6/2019 |
| JP | 2006-083368 A | 3/2006 |
| JP | 2006-184427 A | 7/2006 |
| JP | 2007-284590 A | 11/2007 |
| JP | 2014-181321 A | 9/2014 |
| WO | 2014/185471 A1 | 11/2014 |
| WO | 2018/043548 A1 | 3/2018 |
| WO | 2018/051876 A1 | 3/2018 |

OTHER PUBLICATIONS

Non-Final Office Action dated Jul. 11, 2024, issued in U.S. Appl. No. 17/296,639. (24 pages).
"Thionyl Chloride", SOCl2, CID 24386—PubChem, National Library of Medicine, https://pubchem.ncbi.nlm.nih.gov/compound/Thionyl-choride, accessed Jun. 12, 2024, create date Mar. 27, 2005, section 10.4.2 (Year: 2005). (101 pages).
"Sulfuryl Chloride", SO2Cl2, CID 24648—PubChem, National Library of Medicine, https://pubchem.ncbi.nlm.nih.gov/compound/24648#section=Fire-Hazards, accessed Jun. 13, 2024, create date Sep. 16, 2004, section 9.1.5 (Year: 2004). (75 pages).

* cited by examiner

*Primary Examiner* — Deepak R Rao
(74) *Attorney, Agent, or Firm* — WHDA, LLP

(57) ABSTRACT

A method for producing a halogenated zinc phthalocyanine pigment includes a step of forming a halogenated zinc phthalocyanine crude pigment into a pigment. The halogenated zinc phthalocyanine crude pigment is obtained by deposition of a halogenated zinc phthalocyanine, which is synthesized by using a compound that generates an acid by reacting with water, and the step includes a pretreatment step of heating the halogenated zinc phthalocyanine crude pigment in water to obtain a halogenated zinc phthalocyanine prepigment having a pH of 5.0 or more.

6 Claims, No Drawings

METHOD FOR PRODUCING HALOGENATED ZINC PHTHALOCYANINE PIGMENT

TECHNICAL FIELD

The present invention relates to a method for producing a halogenated zinc phthalocyanine pigment.

BACKGROUND ART

Presently, colored compositions are used in a variety of fields, and examples of the specific usages of the colored compositions include printing inks, paints, coloring agents for resins, coloring agents for fibers, and coloring materials (color filters, toners, and ink let) for IT information recording. Color matters used in the colored compositions are mainly roughly categorized into pigments and dyes, and organic pigments, which are considered to be superior for their coloring power, have drawn much attention.

Organic compounds that constitute organic pigments undergo aggregation of fine particles after synthesis and are in an aggregated state that is referred to as crude. Thus, usually, synthesized organic compounds cannot be directly used as pigments, and are subjected to a pigmentation step for adjusting the particle size. The aggregate (crude) of an organic compound to be formed into a pigment in the pigmentation step is called a crude pigment, and a fine organic pigment can be obtained by grinding the crude pigment by kneading or the like.

As organic pigments, halogenated zinc phthalocyanine pigments that are used in green pixel portions of color filters etc., have gained much attention (for example, see PTL 1).

CITATION LIST

Patent Literature

PTL 1: International Publication No. 2018/043548 pamphlet

SUMMARY OF INVENTION

Technical Problem

An object of the present invention is to provide a novel method for producing a halogenated zinc phthalocyanine pigment, with which pigment particles can be made finer.

Solution to Problem

As a method for synthesizing a halogenated zinc phthalocyanine, for example, a chlorosulfonic acid method, a fusion method, and the like are known. According to these methods, a halogenated zinc phthalocyanine is synthesized by using a compound that generates an acid by reacting with water. A crude pigment (halogenated zinc phthalocyanine crude pigment), which is an aggregate of halogenated zinc phthalocyanine, is obtained by depositing the synthesized halogenated zinc phthalocyanine in water or an acidic solution. According to such a method, in general, an acid derived from the aforementioned compound that generates an acid by reacting with water adheres to the crude pigment; thus, prior to forming the crude pigment into a pigment, washing for removing the acid adhering to the crude pigment is performed. However, the results of examination by the present inventors have revealed that even when the crude pigment is washed to an extent that, the pH of the filtrate is substantially equal to the pH of the water used in washing, the acid still remains inside the crude pigment. The present invention has been made on the basis of such examination results.

That is, one aspect of the present invention relates to a method for producing a halogenated zinc phthalocyanine pigment, the method including a step of forming a halogenated zinc phthalocyanine crude pigment into a pigment. The halogenated zinc phthalocyanine crude pigment used in this method is obtained by depositing a halogenated zinc phthalocyanine, which is synthesized by using a compound that generates an acid by reacting with water, and the aforementioned step includes a pretreatment step of heating the halogenated zinc phthalocyanine crude pigment in water to obtain a halogenated zinc phthalocyanine prepigment having a pH of 5.0 or more.

According to the production method of the aforementioned aspect, the acid encapsulated in the halogenated zinc phthalocyanine crude pigment can be removed, and thus a fine halogenated zinc phthalocyanine pigment can be obtained.

The temperature at which the halogenated zinc phthalocyanine crude pigment is heated in the pretreatment step may be 40° C. or more.

The time for which the halogenated zinc phthalocyanine crude pigment is heated in the pretreatment step may be 1 minute or longer.

In the pretreatment step, after the halogenated zinc phthalocyanine crude pigment is heated in water, the heated halogenated zinc phthalocyanine crude pigment may be washed with water. In addition, the washed halogenated zinc phthalocyanine crude pigment may be subjected to the operation of heating in water and then washing with water repeatedly twice or more.

Advantageous Effects of Invention

According to the present invention, a novel method for producing a halogenated zinc phthalocyanine, with which further micronization of pigment particles is possible, can be provided.

DESCRIPTION OF EMBODIMENTS

Preferable embodiments of the present invention will now be described. However, the present invention is not in any way limited by the embodiments described below.

A method for producing a halogenated zinc phthalocyanine pigment according to one embodiment includes a first step of preparing a halogenated zinc phthalocyanine crude pigment; and a second step of forming the halogenated zinc phthalocyanine crude pigment into a pigment, in which the second step includes a pretreatment step of heating the halogenated zinc phthalocyanine crude pigment in water to adjust the pH of the halogenated zinc phthalocyanine crude pigment to 5.0 or more. Here, the halogenated zinc phthalocyanine crude pigment is obtained by depositing a halogenated zinc phthalocyanine, which is synthesized by using a compound that generates an acid by reacting with water, and the halogenated zinc phthalocyanine is a compound having a structure represented by formula (1) below.

[Chem. 1]

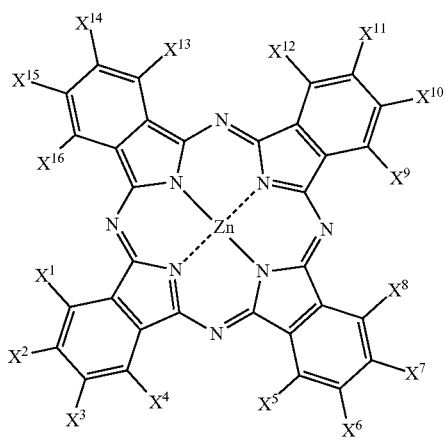

(1)

[In formula (1), $X^1$ to $X^{16}$ each independently represent a hydrogen atom or a halogen atom.]

In the first step, a halogenated zinc phthalocyanine crude pigment is prepared. The halogenated zinc phthalocyanine crude pigment contains one halogenated zinc phthalocyanine or multiple halogenated zinc phthalocyanines among which the number of halogen atoms is different.

Examples of the halogen atom include a fluorine atom, a chlorine atom, a bromine atom, and an iodine atom. The halogenated zinc phthalocyanine preferably contains, as the halogen atom, at least one of a bromine atom and a chlorine atom, and preferably contains a bromine atom. The halogenated zinc phthalocyanine may contain, as the halogen atom, just one or both of a bromine atom and a chlorine atom. In other words, $X^1$ to $X^{16}$ in formula (1) above may each represent a chlorine atom or a bromine atom.

In one embodiment, the average number of bromine atoms in one molecule of the compound represented by formula (1) in the halogenated zinc phthalocyanine crude pigment is less than 13. The average number of bromine atoms may be 12 or less, or 11 or less. The average number of bromine atoms may be 0.1 or more, 6 or more, or 8 or more. The upper limits and the lower limits described above can be freely combined. For example, the average number of bromine atoms may be 0.1 or more but less than 13, may be 8 to 12, or may be 8 to 11. In the description below also, the upper limits and the lower limits described separately may be freely combined.

When the average number of bromine atoms is less than 13, the average number of halogen atoms in one molecule of the compound represented by formula (1) in the halogenated zinc phthalocyanine crude pigment may be 14 or less, 13 or less, less than 13, or 12 or less. The average number of halogen atoms may be 0.1 or more, 3 or more, or 10 or more.

When the average number of bromine atoms is less than 13, the average number of chlorine atoms in one molecule of the compound represented by formula (1) in the halogenated zinc phthalocyanine crude pigment may be 5 or less, 3 or less, 2.5 or less, or less than 2. The average number of chlorine atoms may be 0.1 or more, 0.3 or more, 0.6 or more, 0.8 or more, 1 or more, 1.3 or more, or 2 or more.

In another embodiment, the average number of bromine atoms in one molecule of the compound represented by formula (1) in the halogenated zinc phthalocyanine crude pigment is 13 or more. The average number of bromine atoms may be 14 or more. The average number of bromine atoms may be 15 or less.

When the average number of bromine atoms is 13 or more, the average number of halogen atoms in one molecule of the compound represented by formula (1) in the halogenated zinc phthalocyanine crude pigment may be 13 or more, 14 or more, or 15 or more. The average number of halogen atoms may be 16 or less or 15 or less.

When the average number of bromine atoms is 13 or more, the average number of chlorine atoms in one molecule of the compound represented by formula (1) in the halogenated zinc phthalocyanine crude pigment may be 0.1 or more or 1 or more. The average number of chlorine atoms may be 3 or less, or less than 2.

The number of halogen atoms mentioned above (for example, the number of bromine atoms and the number of chlorine atoms) can be determined, for example, by mass spectrometry of a halogenated zinc phthalocyanine crude pigment by using a matrix-assisted laser desorption/ionization time-of-flight mass spectrometer (JMS-S3000 produced by JEOL Ltd., or the like). Specifically, the numbers of respective halogen atoms can be calculated as relative values per zinc atom from the mass ratio between zinc atoms to the halogen atoms in the halogenated zinc phthalocyanine crude pigment.

The first step includes, for example, a step of synthesizing a halogenated zinc phthalocyanine by using a compound that generates an acid by reacting with water, and a step of obtaining a halogenated zinc phthalocyanine crude pigment by depositing the synthesized halogenated zinc phthalocyanine.

Examples of the method for synthesizing a halogenated zinc phthalocyanine by using a compound that generates an acid by reacting with water include a chlorosulfonic acid method and a fusion method.

An example of the chlorosulfonic acid method is a method that involves dissolving zinc phthalocyanine in a sulfur oxide solvent, such as chlorosulfonic acid, and charging chlorine gas and bromine into the resulting product to perform halogenation. The reaction here is performed at a temperature in the range of 20 to 120° C. for 3 to 20 hours, for example. In the chlorosulfonic acid method, the sulfur oxide solvent, such as chlorosulfonic acid, is the compound that generates an acid by reacting with water. For example, chlorosulfonic acid generates hydrochloric acid and sulfuric acid by reacting with water.

An example of the fusion method is a method that involves halogenating zinc phthalocyanine with a halogenating agent in a melt having a temperature of about 10 to 170° C. and being formed of one compound or two or more compounds that serve as a solvent during halogenation, such as aluminum halide, e.g., aluminum chloride or aluminum bromide, titanium halide, e.g., titanium tetrachloride, alkali metal halide or alkaline earth metal halide such as sodium chloride or sodium bromide (hereinafter referred to as "alkali (earth) metal halide"), or thionyl chloride. In the fusion method, the compound that serves as a solvent during halogenation, such as aluminum halide, titanium halide, alkali (earth) metal halide, or thionyl chloride, is the compound that generates an acid by reacting with water. For example, aluminum chloride generates hydrochloric acid by reacting with water.

A preferable aluminum halide is aluminum chloride. The amount of the aluminum halide added in the aforementioned method that involves using aluminum halide is usually at least three times more and is preferably ten to twenty times more than the amount of zinc phthalocyanine in terms of mole.

An aluminum halide may be used alone; however, combined use of an alkali (earth) metal halide and aluminum halide can further decrease the fusion temperature, and thus provides an operational advantage. A preferable alkali (earth) metal halide is sodium chloride. The amount of the alkali (earth) metal halide added is preferably 1 to 15 parts by mass relative to 10 parts by mass of aluminum halide within the range in which molten salts are generated.

Examples of the halogenating agent include chlorine gas, sulfuryl chloride, and bromine.

The halogenation temperature is preferably 10 to 170° C. and more preferably 30 to 140° C. Furthermore, pressure can be applied to accelerate the reaction. The reaction time may be 5 to 100 hours and is preferably 30 to 45 hours.

The fusion method that uses a combination of two or more of the compounds mentioned above is preferable since the content of halogenated zinc phthalocyanine having a particular halogen atom composition in the synthesized halogenated zinc phthalocyanine can be freely controlled by adjusting the ratio of the chloride, bromide, and iodide in the molten salt or by changing the amount of introducing chlorine gas, bromine, iodine, or the like and the reaction time. Furthermore, according to the fusion method, decomposition of the raw materials during the reaction is less, the yield from the raw materials is superior, and the reaction can be performed in an inexpensive apparatus without using a strong acid.

In this embodiment, the method for charging raw materials, the type of catalyst and the amount thereof used, the reaction temperature, and the reaction time are optimized, and thus a halogenated zinc phthalocyanine having a halogen atom composition different from existing halogenated zinc phthalocyanines can be obtained.

In any of the aforementioned methods, after completion of the reaction, the resulting mixture is put into water or an acidic aqueous solution such as hydrochloric acid so as to settle (deposit) the synthesized halogenated zinc phthalocyanine. During this process, the compound that generates an acid by reacting with water generates the acid. Examples of the acid include hydrochloric acid and sulfuric acid.

The aforementioned deposits may be used as are as the halogenated zinc phthalocyanine crude pigment; however, it is preferable to filter the deposits, wash the filtered deposits with water, sodium hydrogen sulfate water, sodium hydrogen carbonate water, or sodium hydroxide water, wash the resulting product with an organic solvent such as acetone, toluene, methyl alcohol, ethyl alcohol, or dimethylformamide as needed, and then perform a posttreatment such as drying, and to use the resulting product as the halogenated zinc phthalocyanine crude pigment.

The deposits or the deposits after the aforementioned posttreatment may be dry-ground in a grinder such as an attritor, a ball mill, a vibrating mill, a vibrating ball mill, or the like, as needed, and the resulting product may be used as the halogenated zinc phthalocyanine crude pigment. The arithmetic standard deviation of the particle size distribution of the halogenated zinc phthalocyanine crude pigment is, for example, 15 ran or more. The arithmetic standard deviation of the particle size distribution of the halogenated zinc phthalocyanine crude pigment is, for example, 1500 nm or less. When the arithmetic standard deviation of the particle size distribution of the halogenated zinc phthalocyanine crude pigment is within such a range, the acid removing effect in the pretreatment step described below is easily obtained. The arithmetic standard deviation of the particle size distribution of the halogenated zinc phthalocyanine crude pigment can be measured by using a dynamic light scattering particle diameter distribution measurement instrument, and, specifically, can be measured by the following method under the following conditions.

<Method>

In a paint shaker produced by TOYO SEIKI CO., LTD., 2.48 g of a halogenated zinc phthalocyanine crude pigment, 1.24 g of BYK-LPN6919 produced by BYK-Chemie, 1.86 g of UNIDIC ZL-295 produced by DIG Corporation, and 10.92 g of propylene glycol monomethyl ether acetate are dispersed with zircon beads having a diameter of 0.3 to 0.4 mm for 2 hours to obtain a dispersion. After the zircon beads are removed by using a nylon mesh, 0.02 g of the obtained dispersion is diluted with 20 g of propylene glycol monomethyl ether acetate to obtain a particle size distribution measurement dispersion.

<Conditions>

Measurement instrument: dynamic light scattering particle diameter distribution analyzer LB-550 (produced by Horiba Ltd.)

Measurement temperature: 25° C.

Measurement sample: particle size distribution measurement dispersion

Data analysis conditions: particle diameter-based scattering light intensity, dispersion medium refractive index: 1.402

The halogenated zinc phthalocyanine crude pigment obtained in the first step (the halogenated zinc phthalocyanine crude pigment used in the second step) encapsulates acids (hydrochloric acid, sulfuric acid, etc.), and, for example, has a pH of 4.0 or less or may have a pH of 3.3 or less. The pH of the halogenated zinc phthalocyanine crude pigment is, for example, 1.5 or more, and may be 3.5 or more. Here, the pH of the halogenated zinc phthalocyanine crude pigment can be confirmed by mixing 5 g of the halogenated zinc phthalocyanine crude pigment with 5 g of methanol, mixing the resulting mixture with 100 ml of ion exchange water, heating the resulting mixture for 5 minutes to boil, maintaining the boiling state for 5 minutes by further heating, cooling the heated mixture to 30° C. or lower, adjusting the total amount of the mixture to 100 ml by using ion exchange water, filtering the resulting mixture, and measuring the pH of the resulting filtrate at 25° C.

The reason why the halogenated zinc phthalocyanine crude pigment obtained in the first step encapsulates acids (hydrochloric acid, sulfuric acid, etc.) is presumed to be as follows. That is, in a halogenated zinc phthalocyanine, the distance between the center metal, zinc, and the nitrogen atoms on the isoindoline units is large, and thus a large void is present around the center metal (zinc); thus, after nitrogen of the phthalocyanine ring is protonated under acidic conditions, the counter anions (for example, chloride ions) smoothly approach the center metal (zinc), and the counter anions and the center metal (zinc) bond to assume a stable structure. Presumably thus, for example, even when, after the halogenated zinc phthalocyanine is settled, the deposits are washed with water until the pH of the filtrate is substantially equal to the pH of the water used for washing, the acids encapsulated in the deposits (acids derived from the compound that generates an acid by reacting with water, etc.) are not easily removed, and thus acids remain in the crude pigment.

The second step includes, for example, a pretreatment step of heating the halogenated zinc phthalocyanine crude pigment in water to adjust the pH of the crude pigment to 5.0 or more, and a step of micronizing the halogenated zinc phthalocyanine crude pigment (hereinafter may also be referred to as a "halogenated zinc phthalocyanine prepigment") after the pretreatment step by kneading and grinding (micronizing step). Kneading in the micronizing step may involve the use of a kneader, a mix muller, or the like.

In the pretreatment step, heating may be performed after the halogenated zinc phthalocyanine crude pigment is mixed with water, or the crude pigment may be heated by injecting the halogenated zinc phthalocyanine crude pigment into heated water.

The water used in the pretreatment step may be any as long as acids encapsulated in the halogenated zinc phthalocyanine crude pigment can be dissolved, and examples thereof include deionized water, ion exchange water, and ultra pure water. The pH of water at 25° C. may be, for example, 5.5 to 8.5.

The amount of water used may be, for example, 100 parts by mass or more and 10000 parts by mass or less relative to 100 parts by mass of the halogenated zinc phthalocyanine crude pigment. When the amount of water used is equal to or more than the lower limit, the acids encapsulated in the halogenated zinc phthalocyanine crude pigment tend to be more easily removed.

An organic solvent (for example, an organic solvent that can be used in the micronizing step described below) may be mixed in the water. The amount of the organic solvent mixed relative to 100 parts by mass of water is preferably 20 parts by mass or less, more preferably 10 parts by mass or less, and yet more preferably 5 parts by mass or less.

The temperature at which the halogenated zinc phthalocyanine crude pigment is heated (heating temperature) is preferably 40° C. or more, more preferably 60° C. or more, and yet more preferably 70° C. or more from the viewpoint of facilitating removal of acids encapsulated in the halogenated zinc phthalocyanine crude pigment. The heating temperature may be the boiling point of water. That is, in the pretreatment step, the halogenated zinc phthalocyanine crude pigment may be boiled in water. The heating temperature is, for example, equal to or lower than the boiling point of water and may be 100° C. or less.

The time for heating the halogenated zinc phthalocyanine crude pigment (heating time) may be appropriately adjusted depending on the amount of the halogenated zinc phthalocyanine crude pigment and the like, and may be, for example, 1 minute or longer, 5 minutes or longer, or 10 minutes or longer, may be 300 minutes or shorter, 200 minutes or shorter, or 100 minutes or shorter, and may be 1 to 300 minutes. Note that the heating time may be rephrased as a time of retaining the halogenated zinc phthalocyanine crude pigment at that heating temperature (for example 40 to 100° C.). Thus, when the halogenated zinc phthalocyanine crude pigment and water are mixed and then heated, the time needed to increase the temperature (temperature elevation time) is not included in the aforementioned heating time. The temperature elevation time may be, for example, 1 minute to 2 hours.

From the viewpoint of facilitating removal of the acids encapsulated in the halogenated zinc phthalocyanine crude pigment, the wettability of the halogenated zinc phthalocyanine crude pigment relative to water is preferably improved during or before the heating treatment in water (during or before the halogenated zinc phthalocyanine crude pigment is brought into contact with water). An example of the method for improving the wettability of the halogenated zinc phthalocyanine crude pigment relative to water is a method that involves bringing the halogenated zinc phthalocyanine crude pigment into contact with a water-soluble organic solvent, such as methanol. The amount of the water-soluble organic solvent used may be, for example, 1 part by mass or more and 300 parts by mass or less relative to 100 parts by mass of the halogenated zinc phthalocyanine crude pigment.

After the heat treatment in water, the halogenated zinc phthalocyanine crude pigment is preferably washed from the viewpoint of sufficiently removing water that contains acids. Washing may involve washing with cold water (washing with water having a temperature of less than 40° C.) or washing with hot water (washing with water having a temperature of 40° C. or more). Washing may be repeated multiple times (for example, two to five times). Specifically, washing is preferably performed until the pH of the filtrate is substantially equal to (for example, the difference of 0.2 or less) the pH of water used for washing. After washing, operations such as filtering, drying, crushing, and the like may be performed as needed.

In the pretreatment step, from the viewpoint of further removing the acids encapsulated in the halogenated zinc phthalocyanine crude pigment, the washed crude pigment may be repeatedly subjected to the operation of heating in water and washing with water (for example, the operation is repeated twice or more). The heating conditions and the washing conditions for this stage are the same as those described above. Thus, the pretreatment step may be rephrased as a step of adjusting the pH of the halogenated zinc phthalocyanine crude pigment to 5.0 or more by repeating, at least once (preferably three times or more), a series of operation of heating the halogenated zinc phthalocyanine crude pigment in water (preferably at a heating temperature of 40 to 100V; for a heating time of 1 to 300 minutes) and then washing the heated crude pigment with water.

In the pretreatment step, at least a portion of the acids encapsulated in the halogenated zinc phthalocyanine crude pigment is removed. As a result, a halogenated zinc phthalocyanine prepigment having a pH of 5.0 or more is obtained. Here, the pH of the halogenated zinc phthalocyanine prepigment is a pH of a filtrate at 25*C which is obtained by mixing 5 g of the halogenated zinc phthalocyanine prepigment and 5 g of methanol, mixing the resulting mixture with 100 ml of ion exchange water, heating the resulting mixture for 5 minutes to boil, maintaining the boiling state for 5 minutes by further heating, cooling the heated mixture to 30° C. or lower, adjusting the total amount of the mixture to 100 ml by using ion exchange water, and then filtering the resulting mixture.

In the pretreatment step, from the viewpoint of easily obtaining finer pigment particles, the pH of the halogenated zinc phthalocyanine prepigment is preferably adjusted to 6.0 or more and more preferably adjusted to 6.5 or more. The pH of the halogenated zinc phthalocyanine prepigment may be, for example, 3.5 or less or 7.0 or less.

The micronizing step may be a step of kneading the halogenated zinc phthalocyanine prepigment together with an organic solvent, or may be a step of kneading the halogenated zinc phthalocyanine prepigment together with an inorganic salt and an organic solvent. In the micronizing step, water is preferably not used. The amount of the water used may be, for example, 20 parts by mass or less, 10 parts by mass or less, or 5 parts by mass or less relative to 100 parts by mass of the organic solvent.

An organic solvent that does not dissolve the halogenated zinc phthalocyanine prepigment and the inorganic salt can be used as the organic solvent. An organic solvent that can suppress crystal growth is preferably used as the organic solvent. A water-soluble organic solvent is suitable for use as such an organic solvent. Examples of the organic solvent that can be used include diethylene glycol, glycerin, ethylene glycol, propylene glycol, liquid polyethylene glycol, liquid polypropylene glycol, 2-(methoxymethoxy)ethanol, 2-butoxyethanol, 2-(isopentyloxy)ethanol, 2-(hexyloxy) ethanol, diethylene glycol monomethyl ether, diethylene glycol monoethyl ether, diethylene glycol monobutyl ether, triethylene glycol, triethylene glycol monomethyl ether, l-methoxy-2-propanol, 1-ethoxy-2-propanol, dipropylene glycol, dipropylene glycol monomethyl ether, and dipropylene glycol monoethyl ether. The amount of the organic solvent (for example, a water-soluble organic solvent) used is not particularly limited but is preferably 1 to 500 parts by mass relative to 100 parts by mass of the halogenated zinc phthalocyanine prepigment.

In the micronizing step, the halogenated zinc phthalocyanine prepigment may be kneaded while being heated. From the viewpoint of more easily obtaining finer pigment particles, the heating temperature is preferably 40° C. or more, more preferably –0° C. or more, yet more preferably 80° C. or more, and still more preferably 90° C. or more. The heating temperature may be, for example, 150*0 or less.

The kneading time in the micronizing step may be, for example, 1 to 60 hours.

In the micronizing step, when an inorganic salt and an organic solvent are used, a mixture containing the halogenated zinc phthalocyanine pigment, the inorganic salt, and the organic solvent is obtained; however, the organic solvent and the inorganic salt may be removed from this mixture, and a solid matter mainly composed of the halogenated zinc phthalocyanine pigment may be subjected to operations such as washing, filtering, drying, crushing, and the like as needed.

In washing, either cold water or hot water may be used. Washing may be repeated once to five times. When a water-soluble inorganic salt and a water-soluble organic solvent are used, the organic solvent and the inorganic salt can be easily removed by washing with water. If needed, acid washing, alkali washing, or organic solvent washing may be performed.

Examples of drying after washing and filtering include batch-drying and continuous drying that involve removing water and/or solvent of the pigment by performing heating at 80 to 120° C. using a heating source installed in a dryer. Examples of the dryer include a box dryer, a band dryer, and a spray dryer. In particular, spray drying using a spray dryer is preferable since dispersing is easy during paste preparation.

Crushing after drying is performed not to increase the specific surface area or decrease the average particle diameter of primary particles but is performed to pulverize and disintegrate the lump-like pigment obtained when, for example, a box dryer or a band dryer is used for drying. Examples of crushing include crushing by using a mortar, a hammer mill, a disk mill, a pin mill, or a jet mill.

According to the aforementioned production method, a fine halogenated zinc phthalocyanine pigment can be obtained. The present inventors presume the reason why such an effect is obtained as follows. First, when acids are present during pigmentation, acids accelerate aggregation of particles and thus micronization of pigment particles is inhibited. Meanwhile, in the production method described above, acids encapsulated in the crude pigment are removed in the pretreatment step, and thus the influence of acids can be alleviated. Thus, according to the aforementioned method, a fine halogenated zinc phthalocyanine pigment is obtained.

The halogenated zinc phthalocyanine pigment obtained by the aforementioned production method is suitable for use as a green pigment for color filters. In general, contrast and brightness tend to improve as the particles of the pigment used in pixel portions of a color filter become smaller. Thus, when the halogenated zinc phthalocyanine pigment obtained by the aforementioned production method is used as a green pigment for color filters, excellent contrast tends to be obtained, and excellent brightness tends to foe obtained.

The average particle diameter of the primary particles (average primary particle diameter) of the halogenated zinc phthalocyanine pigment obtained by the aforementioned method is, for example, 30 nm or less. According to the aforementioned method, a halogenated zinc phthalocyanine pigment that has an average primary particle diameter of 25 nm or less, for example, can be obtained. The average primary particle diameter of the halogenated zinc phthalocyanine pigment may be 10 nm or more. Here, the average primary particle diameter is an average value of long axes of primary particles, and can be determined by measuring the long axes of the primary particles in a manner similar to measuring the average aspect ratio described below.

The average aspect ratio of the primary particles of the halogenated zinc phthalocyanine pigment is, for example, 1.2 or more, 1.3 or more, 1.4 or more, or 1.5 or more. The average aspect ratio of the primary particles of the halogenated zinc phthalocyanine pigment is, for example, less than 2.0, 1.3 or less, 1.6 or less, or 1.4 or less. Better contrast is obtained by using a halogenated zinc phthalocyanine pigment having such an average aspect ratio.

The halogenated zinc phthalocyanine pigment that has a primary particle average aspect ratio within the range of 1.0 to 3.0 preferably does not contain primary particles having an aspect ratio of 5 or more, more preferably does not contain primary particles having an aspect ratio of 4 or more, and further more preferably does not contain primary particles having an aspect ratio exceeding 3.

The aspect ratios and the average aspect ratio of the primary particles can be measured by the following method. First, particles in a view area are imaged with a transmission electron microscope (for example, JEM-2010 produced by JEOL Ltd.). For each of the primary particles present in a two-dimensional image, an axis that is long (long axis) and an axis that is short (short axis) are measured, and the ratio of the long axis to the short axis is assumed to be the aspect ratio of that primary particle. The average values of the long axes and the short axes are determined for forty primary particles, and the ratio of the long axis to the short axis is calculated using the determined values and is assumed to be the average aspect ratio. In this process, the halogenated zinc phthalocyanine pigment used as a sample is ultrasonically dispersed in the solvent (for example, cyclohexane) and then imaged with a microscope. Alternatively, a scanning electron microscope may be used instead of a transmission electron microscope.

EXAMPLES

The contents of the present invention will now be described in further details through examples and comparative examples that do not limit the present invention.

<Synthesis of Crude Pigment>

(Synthesis of Crude Pigment A1)

Into a 300 ml flask, 91 g of sulfuryl chloride (produced by FUJIFILM Wako Pure Chemical Corporation), 109 g of aluminum chloride (produced by KANTO CHEMICAL CO., INC.), 15 g of sodium chloride (produced by Tokyo Chemical Industry Co., Ltd.), 30 g of zinc phthalocyanine (produced by Die Corporation), and 230 g of bromine (produced by FUJIFILM Wako Pure Chemical Corporation) were charged. The temperature was elevated to 130° C. and retained at 130° C. for 40 hours. After the reaction mixture was extracted into water, the reaction mixture was filtered, washed with water, and dried to obtain a halogenated zinc phthalocyanine crude pigment (crude pigment A1). Washing with water was performed until the difference between the pH of the filtrate and the pH of the water used in washing was ±0.2.

The crude pigment A1 was subjected to mass spectrometry with JMS-S3000 produced by JEOL Ltd., and was confirmed to be a halogenated zinc phthalocyanine having an average of 1.8 chlorine atoms and an average of 13.2 bromine atoms. The delay time for the mass spectrometry was 500 ns, the laser intensity was 44%, and the resolving power value of the peak in m/z=1320 or more and 1360 or less was 31804.

(Synthesis of Crude Pigment A2)

Into a 300 ml flask, 90 g of sulfuryl chloride (produced by FUJIFILM Wako Pure Chemical Corporation), 105 g of aluminum chloride (produced by KANTO CHEMICAL CO., INC.), 14 g of sodium chloride (produced by Tokyo Chemical Industry Co., Ltd.), 27 g of zinc phthalocyanine (produced by DIC Corporation), and 55 g of bromine (produced by FUJIFILM Wako Pure Chemical Corporation) were charged. The temperature was elevated to 130° C. and retained at 130° C. for 40 hours. After the reaction mixture was extracted into water, the reaction mixture was filtered, washed with water, and dried to obtain a halogenated zinc phthalocyanine crude pigment (crude pigment A2). Washing with water was performed until the pH of the filtrate was substantially equal to the pH of the water used in washing.

The crude pigment A2 was subjected to mass spectrometry with JMS-S3000 produced by JEOL Ltd., and was confirmed to be a halogenated zinc phthalocyanine having an average of 2.9 chlorine atoms and an average of 9.3 bromine atoms. The delay time for the mass spectrometry was 510 ns, the laser intensity was 40%, and the resolving power value of the peak in m/z=1820 or more and 1860 or less was 65086.

(Measurement of pH of Crude Pigment A1 and Crude Pigment A2)

Into a 300 ml beaker, 5 g of the crude pigment (crude pigment A1 or A2) and 5 g of methanol were weighed and placed, and the resulting mixture was mixed. Thereto, 100 ml of ion exchange water was weighed and added, the resulting mixture was brought to boil over a period of 5 minutes using a hot stirrer, and boiling was continued for further for 5 minutes. Next, after cooled to 30° C. or less, the mixture was placed in a 100 ml measuring cylinder, the total amount was adjusted to 100 ml by using ion exchange water, and the resulting mixture was filtered. The pH of the filtrate and the specific conductivity were measured. The pH of the crude pigment A1 at 25° C. was 3.7, and the specific conductivity was 163 µs/cm (microsiemens per centimeter). The pH of the crude pigment A2 at 25° C. was 3.4, and the specific conductivity was 193 This confirmed that the crude pigment A1 and the crude pigment A2 encapsulated acids, and the acids could not be removed even when the crude pigment was washed with water until the pH of the filtrate was substantially equal to the pH of the water used for washing. The pH was measured with a personal pH meter PH71 produced by Yokogawa Electric Corporation, and the specific conductivity was measured with SevenEasy S30 produced toy METTLER TOLEDO.

Example 1

(Pretreatment step)

Into a 3 L beaker, 50 g of the crude pigment A1, 50 g of methanol, and 1 L of ion exchange were weighed and placed, and the resulting mixture was heated to 90° C. over a period of 20 minutes with a hot stirrer, and heating at 90° C. was further continued for 10 minutes. Subsequently, the resulting mixture was filtered and washed with water. Washing with water was performed until the pH of the filtrate was substantially equal to the pH of the water used in washing.

Next, the crude pigment (water-containing crude pigment 1) after toeing washed with water was transferred to a 3 L beaker, 1 L of ion exchange water was weighed and placed thereto, the resulting mixture was heated to 90° C. over a period of 20 minutes with a hot stirrer, and heating at 90° C. was further continued for 10 minutes. Subsequently, the resulting mixture was filtered and washed with water to obtain a water-containing crude pigment 2. Washing with water was performed until the pH of the filtrate was substantially equal to the pH of the water used in washing. The obtained water-containing crude pigment 2 was subjected to the aforementioned series of operation (heating in water and washing) once again. That is, the water-containing crude pigment 2 was transferred to a 3 L beaker, 1 L of ion exchange water was weighed and placed thereto, the resulting mixture was heated to 90° C. over a period of 20 minutes with a hot stirrer, and heating at 90° C. was further continued for 10 minutes, followed by filtering and washing with water. Washing with water was performed until the pH of the filtrate was substantially equal to the pH of the water used in washing. As a result, a water-containing crude pigment 3 was obtained. The obtained water-containing crude pigment 3 was dried and crushed to obtain a halogenated zinc phthalocyanine prepigment (prepigment 31).

(Measurement of pH of Prepigment B1)

Into a 300 ml beaker, 5 g of the prepigment B1 and 5 g of methanol were weighed and placed, and the resulting mixture was mixed. Thereto, 100 ml of ion exchange water was weighed and added, the resulting mixture was brought to boil over a period of 5 minutes using a hot stirrer, and boiling was continued further for 5 minutes. Next, after cooled to 30° C. or less, the mixture was placed in a 100 ml measuring cylinder, the total amount was adjusted to 100 ml by using ion exchange water, and the resulting mixture was filtered. The pH and the specific conductivity of the filtrate were measured and were 6.0 at 25° C. and 51 µs/cm, respectively. This confirmed that at least a portion of the acids encapsulated therein was removed from the prepigment 31.

(Micronizing Step)

Into a double-armed kneader, 40 g of the prepigment B1, 400 g of crushed sodium chloride, and 63 g of diethylene glycol were charged, and the resulting mixture was kneaded at 80° C. for 8 hours. The kneaded mixture was extracted into 2 kg of water at 80° C., and stirred for 1 hour. Subsequently, filtering, washing with hot water, drying, and crushing were performed to obtain a green pigment G1.

(Measurement of Average Primary Particle Diameter)

The green pigment G1 was ultrasonically dispersed in cyclohexane and imaged with a microscope, and the average particle diameter of the primary particles was calculated from the average of forty primary particles constituting the aggregates in the two-dimensional image. The average particle diameter of the primary particles was 29 nm.

(Measurement of pH of Green Pigment G1)

Into a 300 ml beaker, 5 g of the green pigment G1 and 5 g of methanol were weighed and placed, and the resulting mixture was mixed. Thereto, 100 ml of ion exchange water was weighed and added, the resulting mixture was brought to boil over a period of 5 minutes using a hot stirrer, and boiling was continued further for 5 minutes. Next, after cooled to 30° C. or less, the mixture was placed in a 100 ml measuring cylinder, the total amount was adjusted to 100 ml by using ion exchange water, and the resulting mixture was filtered. The pH and the specific conductivity of the filtrate were measured and were 6.1 at 25° C. and 46 µS/cm, respectively.

(Evaluation of Contrast and Brightness)

In a paint shaker produced by TOYO SEIKI CO., LTD., 1.65 g of pigment yellow 138 (CHROMOFINE YELLOW 6206EC produced by Dainichiseika Color & Chemicals Mfg. Co., Ltd.), 3.85 g of DISPERBYK-161 (produced by BYK-Chemie), and 11.00 g of propylene glycol monomethyl ether acetate were dispersed together with zircon beads having a diameter of 0.3 to 0.4 mm for 2 hours to obtain a dispersion.

In a paint, shaker, 4.0 g of the aforementioned dispersion, 0.38 g of UNIDIC ZL-295, and 0.22 g of propylene glycol monomethyl ether acetate were added and mixed to obtain a yellow composition (TY1) for toning.

In a paint shaker produced by TOYO SEIKI CO., LTD., 2.48 g the green pigment G1 obtained in Example 1, 1.24 g of BYK-LPN6919 produced by BYK-Chemie, 1.36 g of UNIDIC ZL-295 produced by DIC Corporation, and 10.92 g of propylene glycol monomethyl ether acetate were dispersed together with zircon beads having a diameter of 0.3 to 0.4 mm for 2 hours to obtain a color filter pigment dispersion (MG1).

In a paint shaker, 4.0 g of the color filter pigment dispersion (MG1), 0.98 g of UNIDIC ZL-295 produced by DIC Corporation, and 0.22 g of propylene glycol monomethyl ether acetate were added and mixed to obtain an evaluation composition (CG1) for forming green pixel portions of a color filter.

The evaluation composition (CG1) was applied to a soda glass substrate by spin coating, dried at 90° C. for 3 minutes, and heated at 230° C. for 1 hour. As a result, a glass substrate that has a colored film on a soda glass substrate and is used for evaluating contrast was prepared. The thickness of the colored film obtained by heating at 230° C. for 1 hour was adjusted to 1.8 urn by adjusting the spinning rate during spin coating.

A coating solution obtained by mixing the yellow composition (TY1) for toning and the evaluation composition (CG1) described above was applied to a soda glass substrate by spin coating, dried at 90° C. for 3 minutes, and heated at 230° C. for 1 hour. As a result, a glass substrate that has a colored film on a soda glass substrate and is used for evaluating brightness was prepared. A colored film having a thickness of the colored film having a chromaticity (x, y) of (0.275, 0.570) for a C light source and obtained by heating at 230° C. for 1 hour was prepared by adjusting the mixing ratio of the yellow composition (TY1) for toning and the evaluation composition (CG1) and the spinning rate during spin coating.

The contrast of the colored film on the glass substrate for contrast evaluation was measured with a contrast tester CT-1 produced by TSUBOSAKA ELECTRIC Co., Ltd., and the brightness of the colored film on the glass substrate for brightness evaluation was measured with U-3900 produced by Hitachi High-Tech Corporation. The results are shown in Table 1. Note that the contrast and brightness shown in Table 1 are values based on the contrast and brightness of Comparative Example 1.

Example 2

A prepigment B2 was obtained as in Example 1 except that, in the pretreatment step, the water-containing crude pigment 1 was subjected to the aforementioned series of operation (heating in water and washing) nine times repeatedly. Moreover, the pH and the specific conductivity of the prepigment B2 were measured as in Example 1. The results are shown in Table 1.

A green pigment G2 was obtained as in Example 1 except that the prepigment B2 was used instead of the prepigment B1. Moreover, the average primary particle diameter, the pH, and the specific conductivity of the green pigment G2 were measured as in Example 1. A glass substrate for contrast evaluation and a glass substrate for brightness evaluation were prepared as in Example 1 except that the green pigment G2 was used instead of the green pigment G1, and the contrast and brightness were measured. The results are shown in Table 1.

Examples 3 and 4

Prepigments 33 and B4 were obtained as in Example 1 except that, in the pretreatment step, the heating time in water or the heating temperature was changed as indicated in Table 1. Moreover, the pH and the specific conductivity of the prepigments B3 and B4 were measured as in Example 1. The results are shown in Table 1.

Green pigments G3 and G4 were obtained as in Example 1 except that the prepigment B3 or B4 was used instead of the prepigment B1. Moreover, the average primary particle diameter, the pH, and the specific conductivity of the green pigments G3 and G4 were measured as in Example 1. A glass substrate for contrast evaluation and a glass substrate for brightness evaluation were prepared as in Example 1 except that the green pigment G3 or G4 was used instead of the green pigment G1, and the contrast and brightness were measured. The results are shown in Table 1.

Examples 5 and 6

Green pigments G5 and G6 were obtained as in Example 1 except that, in the micronizing step, the heating time and/or the kneading time during kneading was changed as indicated in Table 1. Moreover, the average primary particle diameter, the pH, and the specific conductivity of the green pigments G5 and G6 were measured as in Example 1. A glass substrate for contrast evaluation and a glass substrate for brightness evaluation were prepared as in Example 1 except that the green pigment G5 or G6 was used instead of the green pigment G1, and the contrast and brightness were measured. The results are shown in Table 1.

Comparative Example 1

A green pigment G7 was obtained by performing a micronizing step as in Example 1 except that the crude pigment A1 was used instead of the prepigment B1. In other words, in Comparative Example 1, the pretreatment step performed in Example 1 was omitted. Moreover, the average primary particle diameter, the pH, and the specific conductivity of the green pigment G7 were measured as in Example 1. A glass substrate for contrast evaluation and a glass substrate for brightness evaluation were prepared as in Example 1 except that the green pigment G7 was used instead of the green pigment G1, and the contrast and brightness were measured. The results are shown in Table 1.

Comparative Example 2

After obtaining a water-containing crude pigment 1 as in Example 1, the obtained water-containing crude pigment 1 was dried and crushed to obtain a halogenated zinc phthalocyanine prepigment (prepigment B8). In other words, in Comparative Example 2, the water-containing crude pigment 1 was not further subjected to heating in water and washing. Moreover, the pH and the specific conductivity of the prepigment B8 were measured as in Example 1. The results are shown in Table 1.

A green pigment G8 was obtained as in Example 1 except that the prepigment B8 was used instead of the prepigment G1. Moreover, the average primary particle diameter, the pH, and the specific conductivity of the green pigment G8 were measured as in Example 1. A glass substrate for contrast evaluation and a glass substrate for brightness evaluation were prepared as in Example 1 except that the green pigment G8 was used instead of the green pigment G1, and the contrast and brightness were measured. The results are shown in Table 1.

Example 7

A prepigment B9 was obtained by performing a pretreatment of a crude pigment as in Example 1 except that the crude pigment A2 was used instead of the crude pigment. A1. Moreover, the pH and the specific conductivity of the prepigment B9 were measured as in Example 1. The results are shown in Table 2.

A green pigment G9 was obtained as in Example 1 except that the prepigment B9 was used instead of the prepigment. B1. Moreover, the average primary particle diameter, the pH, and the specific conductivity of the green pigment G9 were measured as in Example 1. A glass substrate for contrast evaluation and a glass substrate for brightness evaluation were prepared as in Example 1 except that pigment yellow 185 (Paliotol Yellow D1155 produced by BASF) was used instead of pigment yellow 138 (CHROMOFINE YELLOW 6206EC produced by Dainichiseika Color & Chemicals Mfg. Co., Ltd.), that the green pigment G9 was used instead of the green pigment G1, and that the chromaticity (x, y) of the colored film was adjusted to (0.230, 0.670), and the contrast and brightness were measured. The results are shown in Table 2.

Comparative Example 3

A green pigment G10 was obtained by performing a micronizing step as in Example 7 except that the crude pigment A2 was used instead of the prepigment B9. In other words, in Comparative Example 3, the pretreatment step performed in Example 7 was omitted. Moreover, the average primary particle diameter, the pH, and the specific conductivity of the green pigment G10 were measured as in Example 7. A glass substrate for contrast evaluation and a glass substrate for brightness evaluation were prepared as in Example 7 except that the green pigment G10 was used instead of the green pigment G9, and the contrast and brightness were measured. The results are shown in Table 2.

TABLE 1

| | | Pretreatment step | | | | | Micronizing step | | | | Characteristic values | |
|---|---|---|---|---|---|---|---|---|---|---|---|---|
| | | | | | | | | | | | Monochromatic evaluation: film thickness = 1.8 μm Contrast Std. ratio | Y138 toning evaluation: (0275, 0.570) Brightness Std. ratio |
| | Crude pigment | Temperature (° C.) | Time (min) | Number of times performed (No.) | pH after pretreatment | Specific conductivity after pretreatment (μS/cm) | Temperature (° C.) | Time (h) | pH after micronizing | Specific conductivity after micronizing (μS/cm) | Primary particle diameter (nm) | | |
| Example 1 | A1 | 90 | 10 | 3 | 6.0 | 51 | 80 | 8 | 6.1 | 46 | 29 | 109% | 104.4% |
| Example 2 | A1 | 90 | 10 | 10 | 6.9 | 25 | 80 | 8 | 6.9 | 23 | 26 | 117% | 105.3% |
| Example 3 | A1 | 90 | 30 | 3 | 6.1 | 42 | 80 | 8 | 6.1 | 36 | 28 | 110% | 104.4% |
| Example 4 | A1 | 70 | 10 | 3 | 5.7 | 69 | 80 | 8 | 5.7 | 61 | 30 | 107% | 104.3% |
| Example 5 | A1 | 90 | 10 | 3 | 6.0 | 51 | 60 | 15 | 6.0 | 50 | 27 | 110% | 104.4% |
| Example 6 | A1 | 90 | 10 | 3 | 6.0 | 51 | 100 | 8 | 6.1 | 42 | 30 | 110% | 104.1% |
| Comparative Example 1 | A1 | — | — | — | — | — | 80 | 8 | 3.7 | 134 | 34 | Std. | Std. |
| Comparative Example 2 | A1 | 90 | 10 | 1 | 4.2 | 114 | 80 | 8 | 4.6 | 88 | 32 | 102% | 100.9% |

TABLE 2

| | | Pretreatment step | | | | | Micronizing step | | | | | Characteristic values | |
|---|---|---|---|---|---|---|---|---|---|---|---|---|---|
| | Crude pigment | Temperature (° C.) | Time (min) | Number of times performed (No.) | pH after pretreatment | Specific conductivity after pretreatment (μS/cm) | Temperature (° C.) | Time (h) | pH after micronizing | Specific conductivity after micronizing (μS/cm) | Primary particle diameter (nm) | Monochromatic evaluation: film thickness = 1.8 μm Contrast Std. ratio | Y185 toning evaluation: (0.230, 0.670) Brightness Std. ratio |
| Example 7 | A2 | 90 | 10 | 3 | 5.8 | 67 | 80 | 8 | 5.9 | 54 | 27 | 139% | 103.5% |
| Comparative Example 3 | A2 | — | — | — | — | — | 80 | 8 | 3.4 | 167 | 31 | Std. | Std. |

The invention claimed is:

1. A method for producing a halogenated zinc phthalocyanine pigment from a halogenated zinc phthalocyanine crude pigment, the method comprising:
    providing the halogenated zinc phthalocyanine crude pigment synthesized from a compound that generates an acid by reacting with water followed by deposition; and
    a pretreatment step of heating the halogenated zinc phthalocyanine crude pigment in water to obtain a halogenated zinc phthalocyanine prepigment having a pH of 5.0 or more.

2. The method according to claim 1, wherein, in the pretreatment step, the halogenated zinc phthalocyanine crude pigment is heated at a temperature of 40° C. or more.

3. The method according to claim 1, wherein, in the pretreatment step, the halogenated zinc phthalocyanine crude pigment is heated for 1 minute or longer.

4. The method according to claim 1, wherein, in the pretreatment step, after the halogenated zinc phthalocyanine crude pigment is heated in water, the heated halogenated zinc phthalocyanine crude pigment is washed with water.

5. The method according to claim 4, wherein, in the pretreatment step, operation of subjecting the washed halogenated zinc phthalocyanine crude pigment to heating in water and then washing with water is performed repeatedly twice or more.

6. The method according to claim 1, wherein the compound that generates the acid is selected from the group consisting of sulfur oxide, aluminum halide, titanium halide, alkali (earth) metal halide, and thionyl chloride.

* * * * *